(12) United States Patent
Almena Perea et al.

(10) Patent No.: US 7,531,697 B2
(45) Date of Patent: May 12, 2009

(54) PROCESS FOR THE PREPARATION OF AROMATIC ALDEHYDES

(75) Inventors: Juan Jose Almena Perea, Hanau (DE); Axel Monsees, Frankfurt (DE); Renat Kadyrov, Frankfurt (DE); Thomas Riermeier, Ober-Ramstadt (DE); Kai Rossen, Hanau (DE); Wolf-Ruediger Krahnert, Obertshausen (DE); Matthias Beller, OB Nienhagen (DE); Stefan Klaus, Rostock (DE); Alexander Zapf, Rostock (DE)

(73) Assignee: Degussa GmbH, Duesseldorf (DE)

( * ) Notice: Subject to any disclaimer, the term of this patent is extended or adjusted under 35 U.S.C. 154(b) by 0 days.

(21) Appl. No.: 11/908,446

(22) PCT Filed: Mar. 2, 2006

(86) PCT No.: PCT/EP2006/060387

§ 371 (c)(1),
(2), (4) Date: Sep. 12, 2007

(87) PCT Pub. No.: WO2006/103148

PCT Pub. Date: Oct. 5, 2006

(65) Prior Publication Data

US 2008/0188691 A1    Aug. 7, 2008

(30) Foreign Application Priority Data

Mar. 30, 2005    (DE) .................. 10 2005 014 822

(51) Int. Cl.
 *C07C 45/50*    (2006.01)
(52) U.S. Cl. ..................... 568/429; 568/454
(58) Field of Classification Search .............. 568/454
 See application file for complete search history.

(56) References Cited

U.S. PATENT DOCUMENTS 7,148,176 B2    12/2006  Beller et al.

FOREIGN PATENT DOCUMENTS

DE    32 42 582    5/1984
JP    10330307    12/1998

*Primary Examiner*—Sikarl A Witherspoon
(74) *Attorney, Agent, or Firm*—Oblon, Spivak, McClelland, Maier & Neustadt, P.C.

(57)    ABSTRACT

(Hetero)aromatic are prepared from halogen-substituted (hetero)aromatic compounds in the presence of a base and a palladium catalyst having a nonpyrophoric monodentate phosphane ligand. The phosphane ligand structure includes two radical groups having a tertiary carbon attached directly to phosphorous and one radical group having a primary carbon attached to the phosphorous.

12 Claims, 10 Drawing Sheets

PROCESS FOR THE PREPARATION OF AROMATIC ALDEHYDES

The present invention is aimed at a process for the preparation of (hetero)aromatic . In particular, the process according to the invention comprises the preparation of (hetero)aromatic starting from Hal'-substituted (hetero)aromatics in the presence of catalytic amounts of palladium complexes.

BACKGROUND OF THE INVENTION

Aromatic are important starting substances for the preparation of organic bioactive agents or their intermediates, since these can readily be employed in C-C coupling reactions, reductions or in other derivatizations on account of the reactive aldehyde function [Organikum, 21st edition; Wiley-VCH Verlag, 2001 pages 456-622 (ISBN 3-527-29985-8)].

The palladium-catalysed carbonylations of aryl bromides or iodides for the production of aromatic carboxylic acids [L. Cassar, M. Foa, A. Gardano, J. Organomet. Chem. 1976, 121, $C_{55}$], esters [A. Schoenberg, I. Bartoletti, R. F. Heck, J. Org. Chem. 1974, 39, 3318; J. K. Stille, P. K. Wong, ibid., 1975, 40, 532; M. Hidai, T. Hikita, Y. Wada, Y. Fujikura, Y. Uchida, Bull. Chem. Soc. Jpn. 1975, 48, 2075; T. Ito, K. Mori, T. Mizoroki, A. Ozaki, ibid., 1975, 48, 2091], amides, [A. Schoenberg, R. F. Heck, J. Org. Chem. 1974, 39, 3327], α-oxo amides [T. Kobayashi, M. Tanaka, J. Organomet. Chem. 1982, 233, $C_{64}$; F. Ozawa, H. Soyama, H. Yanagihara, I. Aoyama, H. Takino, K. Izawa, T. Yamamoto, A. Yamamoto, J. Am. Chem. Soc. 1985, 107, 3235], α-oxo esters [M. Tanaka, T. A. Kobayashi, F. Skakura, N. Itatani, S. Danno, K. Zushi, J. Mol. Cat. 1985, 32, 115; B. Morin, A. Hirschauer, F. Hugues, D. Commereuc, Y. Chauvin, J. Mol. Cat. 1986, 34, 317] und α-oxo acids [M. Tanaka, T. A. Kobayashi, T. Sakakura, J. Chem. Soc., Chem. Commun. 1985, 837] are known. In particular, the preparation of substituted benz is of interest on account of the further possibilities of use as synthesis units.

In the literature, the reductive palladium-catalysed carbonylation of halogenated aromatics, heterocycles and vinyls is mentioned for the first time by Heck et al. 1974 [A. Schoenberg, R. F. Heck, J. Am. Chem. Soc. 1974, 96, 7761-7764]. The authors observed that the reaction is essentially restricted to aryl halides, which can only undergo a β-hydride elimination with difficulty. The reaction conditions described extend over a large temperature range (80-150° C.), the dehalogenation mentioned beforehand being able to increase with temperature in a substrate-dependent manner. Pressures of over 80 bar ($CO/H_2$ 1:1) likewise increase the yields.

In the same year, a corresponding patent was filed [U.S. Pat. No. 3,960,932, R. F. Heck, 1974]. Stille et al. were able to convert a series of organic halides into the corresponding in the presence of $Bu_3SnH$ and Pd catalyst [V. P. Baillard-Geon, J. K. Stille, J. Am. Chem. Soc. 1983, 105 (24), 7175-7176]. The process has the advantage that the corresponding result even in the presence of other reactive functional groups.

In DE 3242582, EP 244328 and EP 244329, processes for the palladium-catalysed conversion of haloaromatics, in particular bromo- and iodoaromatics, to aromatic in the presence of synthesis gas are disclosed. In these specifications, mainly a few process technology details are emphasized. In JP 10-330307, the palladium-catalysed reductive carbonylation of bromo- or iodoaromatics in the presence of a palladium catalyst is likewise demonstrated. As a monodentate ligand, tris-tert-butylphosphane is employed. It is reported that this ligand especially helps to achieve unexpectedly high yields of product. The ligand used, however, is pyrophoric and therefore cannot be employed advantageously on a large scale.

DE 10037961 generally discloses adamantyl-substituted phosphane compounds as ligands for, inter alia, carbonylation reactions of haloaromatics. Application to Hal'-substituted (hetero)aromatics in reductive carbonylation has, however, not been explicitly described here.

The object of the present invention was therefore to make available a process which is suitable, in particular on the industrial scale, for the conversion of Hal'-substituted (hetero)aromatics to aromatic in a more advantageous manner compared to the prior art. Very particularly, the process in mind should have advantages with respect to yield, by-product spectrum and handle-ability of the compounds, also from industrial safety points of view. Moreover, seen from the economic and ecological standpoint, it should be superior to the prior art processes.

SUMMARY OF THE INVENTION

These and other objects not mentioned in greater detail but resulting from the prior art in an obvious manner are achieved by a process which is the subject of the present claim 1. Preferred embodiments of the process according to the invention are protected in the Subclaims 2 to 8.

As a result of carrying out a process for the preparation of (hetero)aromatic from Hal'-substituted (hetero)aromatics and CO and $H_2$ in the presence of a base and of a palladium catalyst having a monodentate phosphane ligand of the general formula (I)

where $R^1$ and $R^2$ independently of one another are ($C_5$-$C_{20}$)-alkyl, where the C atom which is bonded to the phosphorus is a tertiary centre and $R^3$ is a primary, optionally linear ($C_3$-$C_{20}$)-alkyl radical, the objects set are achieved in a manner which is simple, but for that no more obvious and particularly advantageous compared to the prior art. By means of the variation according to the invention of the ligand, the reaction considered can be decisively improved, which especially against the background of the preparation of on the industrial scale saves costs and thus helps to contribute to the better ecological and economic utilization of the substances employed. In spite of the total alkyl substitution of the phosphorus ligands, these are not at all pyrophoric and also readily handleable on a large scale.

DETAILED DESCRIPTION OF THE INVENTION

Suitable phosphane ligands of the general formula (I) are known to the person skilled in the art in principle from DE 10037961. It has turned out that the presence of two tertiary alkyl radicals and a primary alkyl radical on the phosphorus affords particularly good ligands for the reaction according to the invention. Particularly preferred phosphanes are those of the general formula (I), which possess two polycyclic and one primary, optionally linear alkyl radical. As polycyclic radicals, the adamantyl radical is preferred. As optionally linear alkyl radicals, ($C_3$-$C_{20}$)-alkyl radicals, such as, for example, n-butyl, n-pentyl, n-hexyl radicals, are suitable here. A phosphane ligand having two adamantyl radicals and an n-butyl radical ($BuPAd_2$) on the phosphorus is very particularly preferred.

The reaction according to the invention preferably proceeds in the presence of a base, which in the catalytic reaction cycle makes sure that resulting protons can be trapped. In principle, the person skilled in the art is free in the choice of a suitable basic compound. Preferably, this, however, can be inexpensive inorganic or organic bases. Suitable inorganic bases preferably to be employed are, in particular, carbonates, hydrogencarbonates, phosphates, mono- or dihydrogenphosphates or hydroxides of the alkali metals or alkaline earth metals. Very particularly preferred are those selected from the group consisting of $K_3PO_4$, $K_2HPO_4$, $K_2CO_3$, $Cs_2CO_3$, NaOH, KOH, and the like. Organic bases preferably to be employed are alkali metal or alkaline earth metal salts of weak organic acids, such as, for example, acetic acid, formic acid, propionic acid, and the like. Further organic bases preferably to be employed are nitrogen-containing organic molecules such as, for example, those selected from the group consisting of $NEt_3$, $N(n-Bu)_3$, DABCO® (1,4-diazabicyclo[2,2,2]octane), DBU® (1,8-diazabicyclo[5,4,0]undec-7-ene, N,N-dimethylglycine ethyl ester, pyridine, tetramethylguanidine TMEDA, hexamethylenetetramine, and the like. Further preferred bases are amines supported on oligomers and polymers and their derivatives (such as, for example, guanidines).

Figure 1:
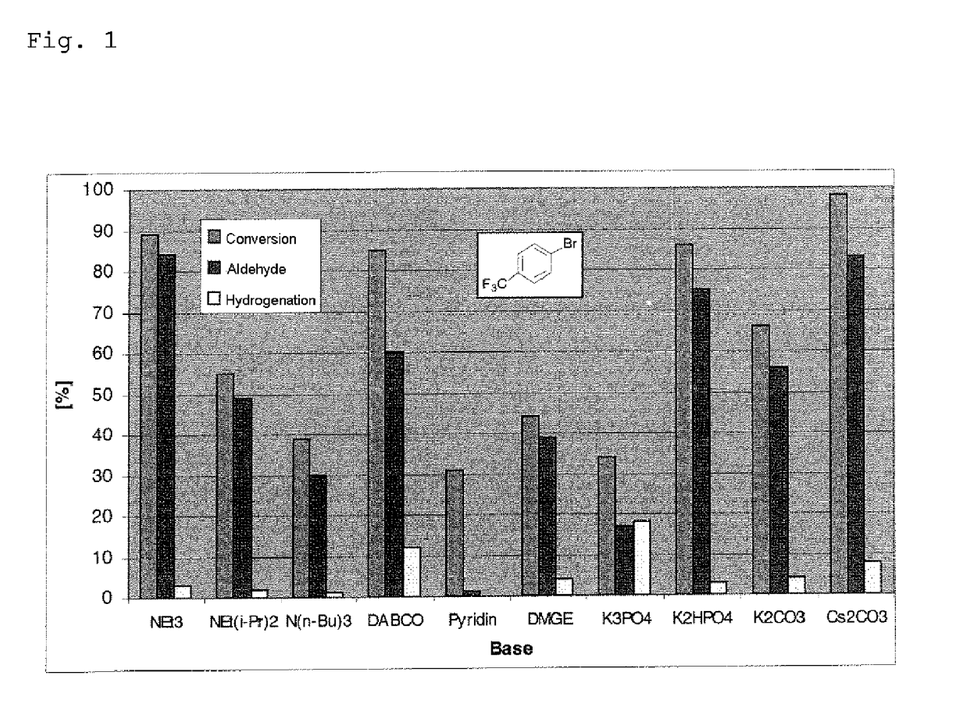
FIGS. 1 and 2 show the experimental results for p—$CF_3$-$C_6H_4$—Br.
Figure 6:
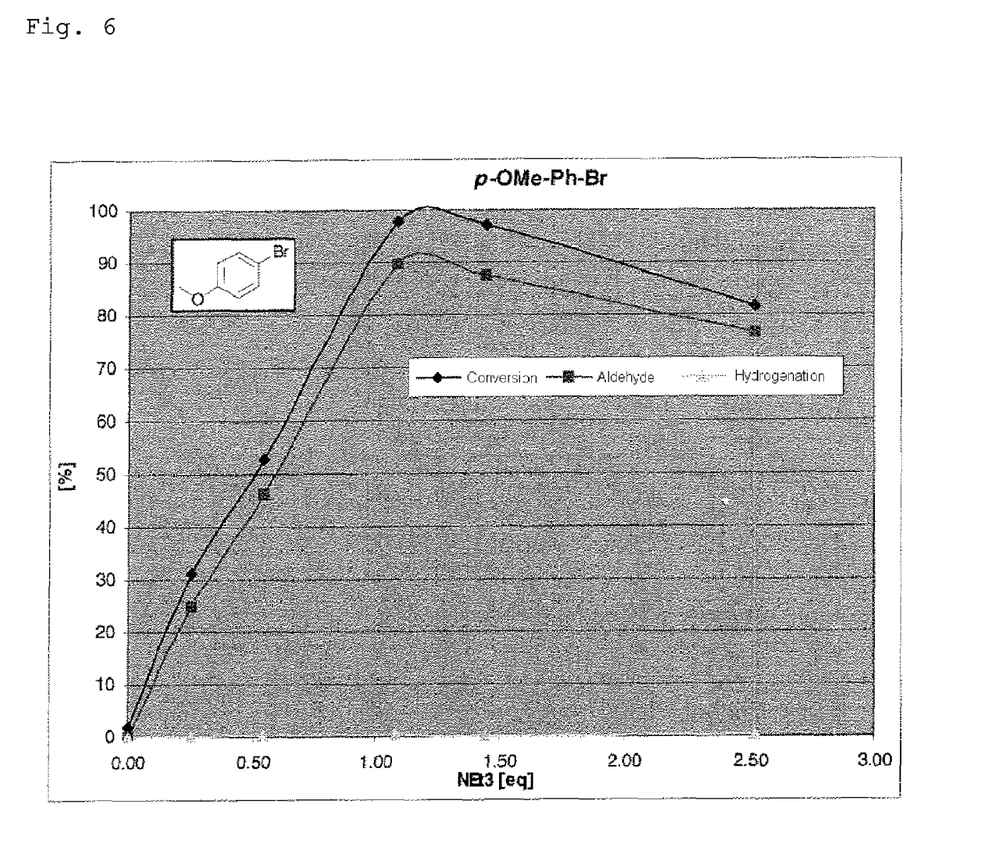
Figure 7:
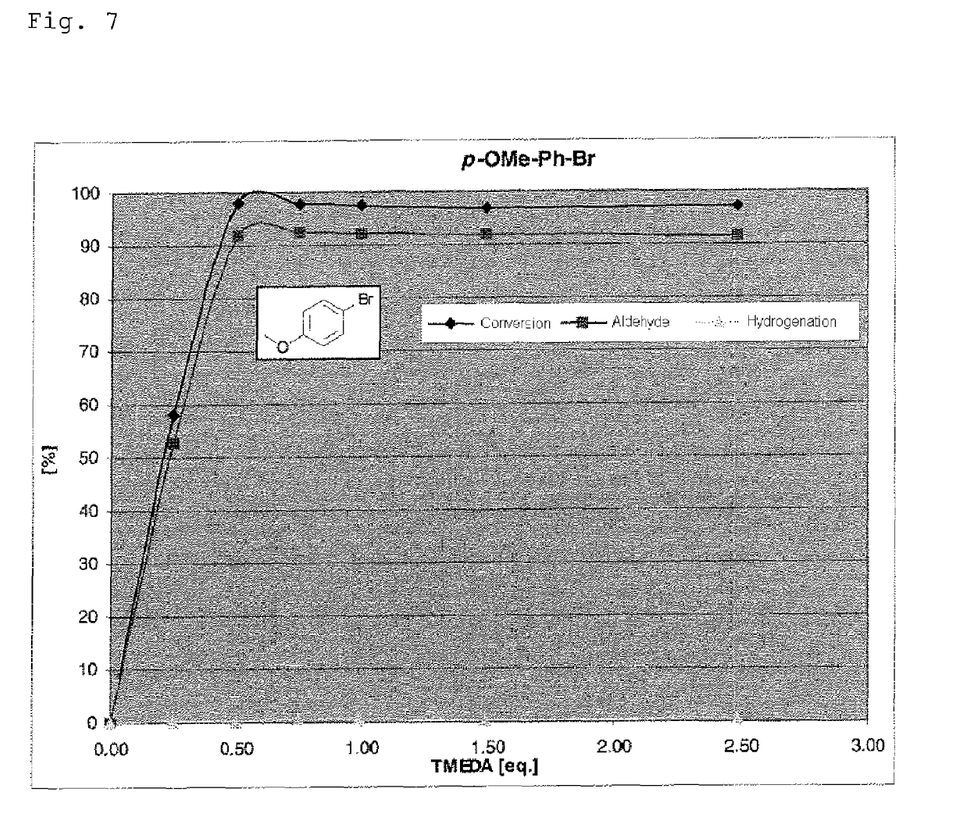

In FIG. 1, experimental results for the four-hour reaction of p-$CF_3$—$C_6H_4$—Br according to the general working procedure are shown for various bases in toluene at 100° C. The amount of the base employed can be freely chosen by the person skilled in the art, where amounts of around 1 base equivalent ±0.5 are to be preferred (FIGS. 6 and 7—conditions: 2 mmol of 4-methoxybromobenzene, 0.33 mol % of Pd(OAc)$_2$, 1 mol % of $BuPAd_2$, 2 ml of toluene, 100° C., 16 h, 5 bar of CO/$H_2$).

Figure 2:
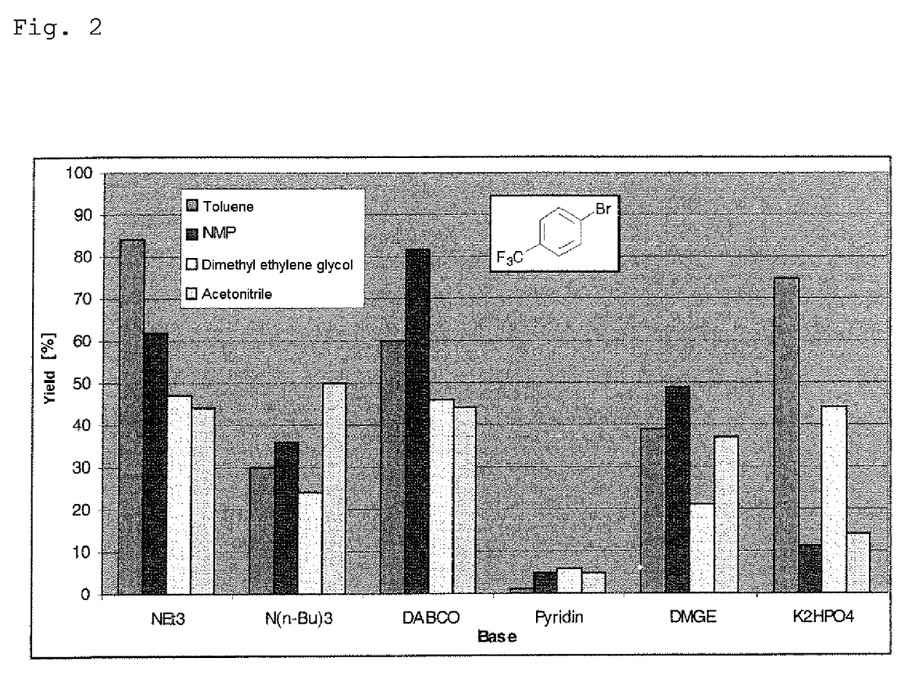

In principle, the person skilled in the art is free in the choice of the solvent in which he would like to carry out the reaction according to the invention. On account of the fact that the starting substances are often present in liquid form, in this respect the use of a solvent can also be dispensed with. If, however, the use of solvents in the reaction according to the invention is desired, it is advantageous to use those solvents which dissolve the employed components of the reaction correspondingly well and otherwise prove inert to the reaction according to the invention. Those suitable are hydrocarbons, in particular aromatic hydrocarbons and their perfluorinated derivatives, ethers, carboxylic acid amides, carboxylic acid esters, thioethers, carbonates, nitriles, halogenated benzenes, and the like. Other inert solvents are ionic or supercritical liquids, which should already be known to the person skilled in the art (for ionic liquids: Wasserscheid, P.; Welton, T.; Editors. Germany. (2003), 364 pp. Publisher: (Wiley-VCH Verlag GmbH & Co. KGaA, Weinheim, Germany); for supercritical liquids: Jessop, P. G.; Ikariya, T. Noyori, R. Science 1995, 269, 1065-1069; Chem Rev 1999, 99, 475-493; Chem. Commun. 1999, 1235-1236). Preferred solvents are those selected from the group consisting of hexane, heptane, octane, NMP (N-methylpyrrolidone, DMGE (dimethyl glycol ether), toluene, anisole, benzene, chlorobenzene, DMF (dimethylformamide), DMAC (dimethylacetamide), 1,4-dioxane, MTBE, THF, acetonitrile, benzonitrile, ethyl acetate, isopropyl acetate, dibutyl ether, dimethyl carbonate, diethyl carbonate, dipropyl carbonate and the like. FIG. 2 shows the results for a selection of solvents when used in the reaction according to the invention. The examples shown have been obtained in the solvent-base combination indicated according to the general working procedure in a reaction at 100° C. for four hours.

Figure 5:
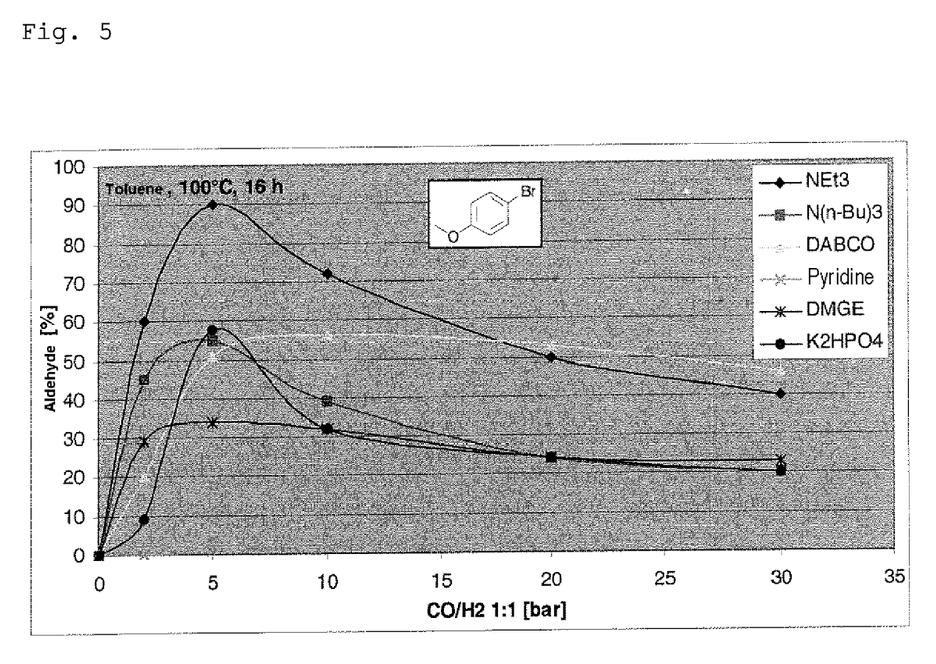

The person skilled in the art can determine at which CO pressure the reaction according to the invention is carried out. It has surprisingly proved that CO pressures which are too high are rather counterproductive for the reaction according to the invention, such that a pressure in the range from 0.05 to 10 MPa, preferably 0.05 to 2 MPa, and very particularly preferably 0.05 to 1.5 MPa, is preferably set. The pressure indication relates here to the pressure of CO in the reaction mixture (FIG. 5). The pressure of $H_2$ can be adjusted accordingly by means of the preferred mixing ratio of CO and $H_2$ stated below.

The mixing ratio between CO and $H_2$ can likewise be adjusted by the person skilled in the art in relation to the reaction in mind. Preferably, a mixing ratio is employed which varies around the range from 1:10 to 10:1. A more preferred mixing ratio (molar ratio) is one of 1:5 to 5:1, further preferably of 1:2 to 2:1. Very particularly preferably, a mixing ratio of 1.25:1 to 1:1.25 of CO to $H_2$ is employed in the reaction according to the invention. The use of synthesis gas in this connection is extremely preferred.

Figure 8:
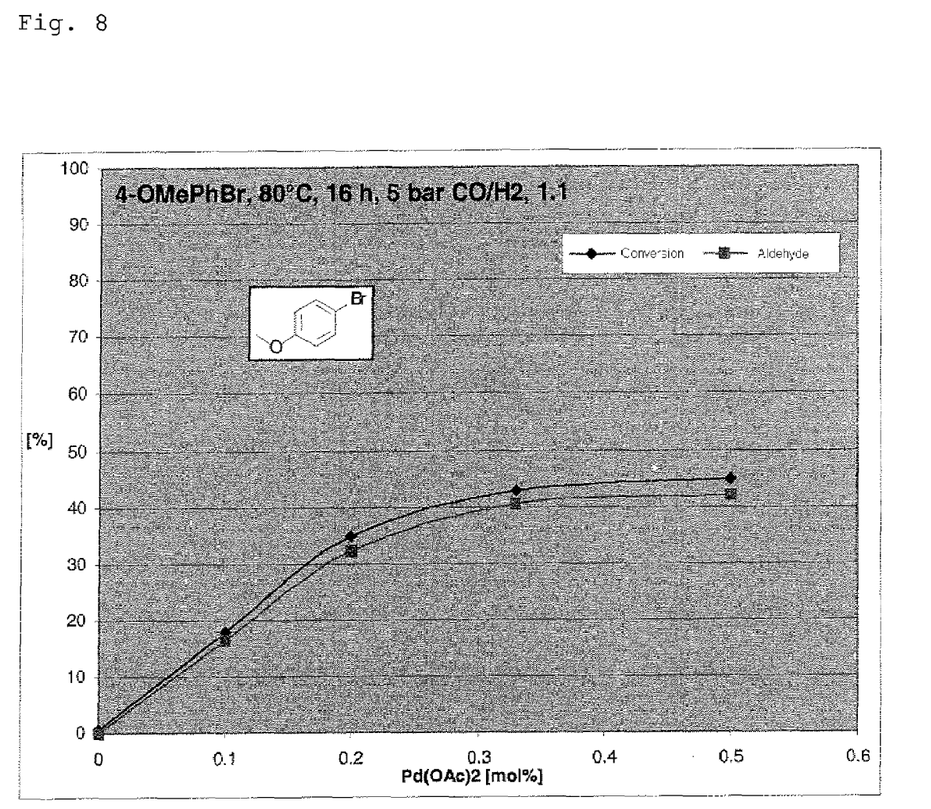
Figure 9:
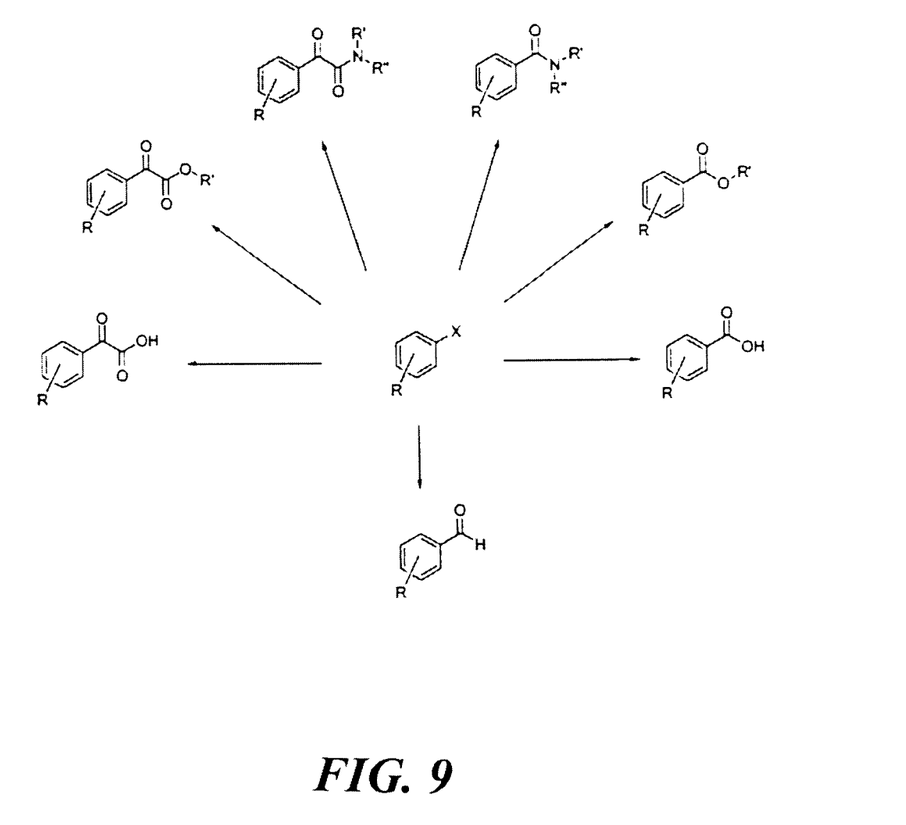
FIG. 9 shows carbonylation reactions of aryl halides.
Figure 10:
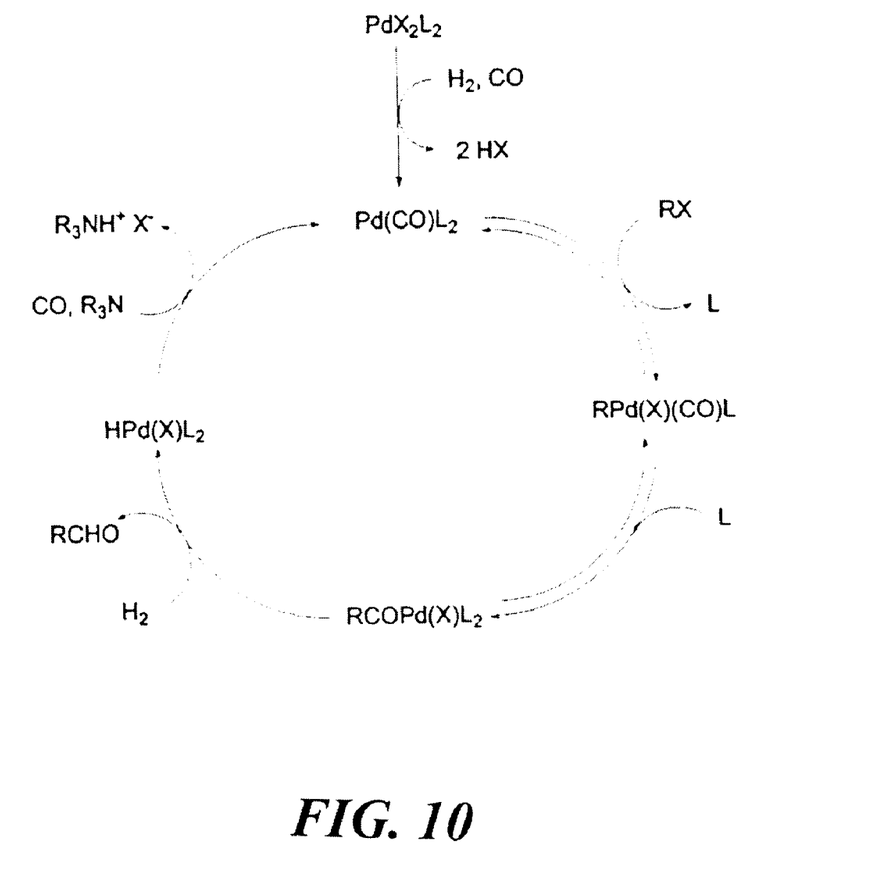
FIG. 10 shows the mechanism of Pd-catalyzed carbonylation by Heck.

With respect to the amount of catalyst to be employed based on the substrate, it can be noted that in principle a higher amount of catalyst also helps to achieve better conversions. The amount of catalyst which has to be employed is preferably in the range from 0.001 mol % to 10 mol % based on the (hetero)aromatics employed. Further preferably, the use of the catalyst lies in the range from 0.01 mol % to 1 mol % and very particularly preferably in the range from 0.05 mol % to 0.5 mol % (FIG. 8—conditions: (2 mmol of 4-methoxybromobenzene, Pd(OAc)$_2$/BuPAd$_2$ 1:3, 1.1 eq. of $NEt_3$, 2 ml of toluene, 80° C., 16 h, 5 bar of CO/$H_2$).

It is generally known that the homogeneous palladium catalyst system can be stabilized against the deposition of palladium metal by means of an increased amount of phosphane. However, it has turned out that with an amount of phosphane which is too high in comparison to the palladium, the achievable conversion of the (hetero)-aromatics decreases. Therefore, the palladium:phosphane ratio (molar ratio) in the reaction according to the invention can advantageously lie in a range from 1:0.1 to 1:20, preferably between 1:1 and 1:10 and very particularly preferably in a range between 1:1 and 1:8.

Figure 3:
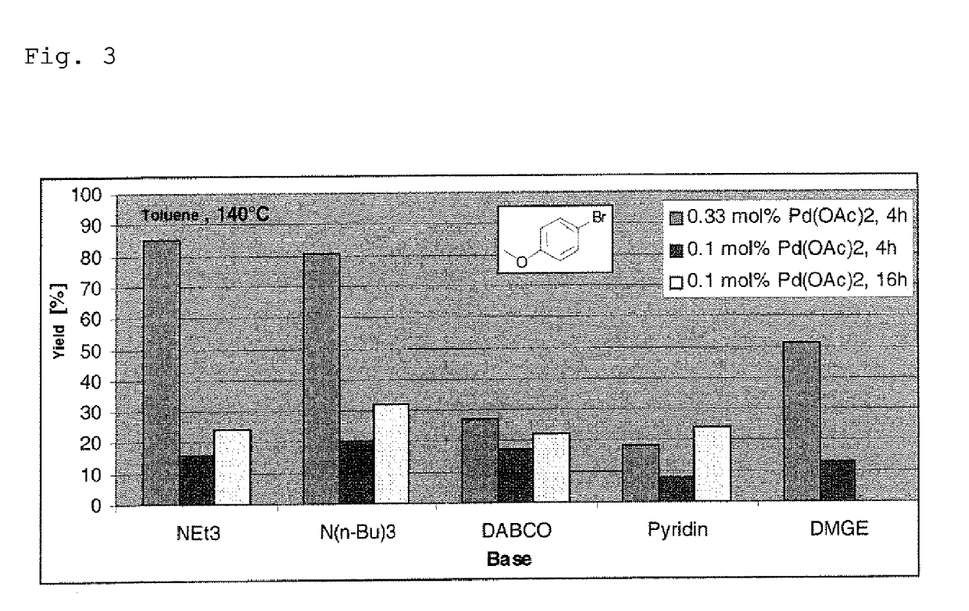
FIGS. 3-8 show experimental results for p—$CH_3$—O—$C_6H_4$—Br.
Figure 4:
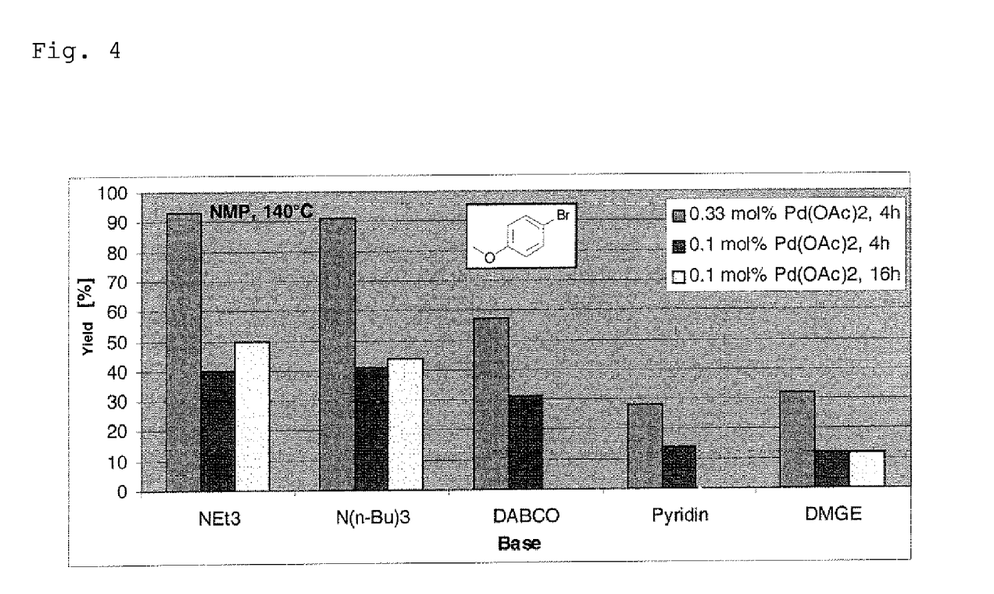

The temperature which is to be set during the reaction can be determined by the person skilled in the art. It should be so high that the envisaged reaction proceeds in sufficiently quick time, but if possible so low that the by-product spectrum can be kept as low as possible in the reaction according to the invention. It has turned out that a temperature of greater than 50° C. and less than 200° C. is to be preferred. A temperature range of greater than 70° C. and less than 170° C. is very particularly preferred. With respect to different systems, the results obtained analogously to the general working procedure are shown in FIGS. 3 and 4.

The expression (hetero)aromatics is to be interpreted such that both aromatics and heteroaromatics are jointly included. As Hal'-substituted (hetero)aromatics, all compounds suitable to the person skilled in the art for this purpose can be selected, preferably Hal'-monosubstituted (hetero)aromatics are to be employed. The use of bromo- or chloro(hetero) aromatics on the industrial scale is further preferred, since iodo(hetero)aromatics as a rule are the dearer starting substances. The Hal'-substituted (hetero)aromatics can in this case preferably be appropriately substituted $(C_6-C_{18})$-aryl-, $(C_3-C_{18})$-heteroaryl compounds.

The palladium catalyst can be prepared, for example, in situ by reaction of a palladium(0) compound or of a palladium (II) salt or of an appropriate pre-complex with the ligands of the general formula (I). Moreover, a palladium-ligand complex compound can be obtained by reaction of a metal salt or of an appropriate pre-complex with the ligands of the general formula (I) and subsequent isolation.

Examples of the metal salts are metal chlorides, bromides, iodides, cyanides, nitrates, acetates, trifluoroacetates, acetylacetonates, hexafluoroacetylacetonates, tetrafluoro-borates or triflates of palladium.

Examples of appropriate pre-complexes are:
cyclooctadienepalladium chloride, cyclooctadienepalladium iodide, 1,5-hexadienepalladium chloride, 1,5-hexadienepalladium iodide, bis(dibenzylideneacetone)palladium(0), tris(dibenzylideneacetone)dipalladium(0)
bis(acetonitrile)palladium(II) chloride,
bis(acetonitrile)palladium(II) bromide,
bis(benzonitrile)palladium(II) chloride,
bis(benzonitrile)palladium(II) bromide,
bis(benzonitrile)palladium(II) iodide, bis(allyl)palladium, bis(methallyl)palladium, allylpalladium chloride dimer, methallylpalladium chloride dimer,
tetramethylethylenediaminepalladium dichloride,
tetramethylethylenediaminepalladium dibromide,
tetramethylethylenediaminepalladium diiodide,
tetramethylethylenediaminepalladium dimethyl.

In the present invention, a procedure is preferably used in which substrate:palladium catalyst:ligand in a ratio of about 300:1:3 is mixed with the appropriate amount of toluene and base in an autoclave. Subsequently, the autoclave is flushed a number of times with, for example, synthesis gas and the mixture is heated at a synthesis gas pressure of, for example, 20 bar to, preferably, 95-105° C. The reaction mixture is left at this pressure for approximately 4 hours at above the set temperature. After the mixture has cooled, it is filtered off and the filtrate is worked up by processes known to the person skilled in the art. The reaction mixture, however, is generally so pure that it can be employed immediately in subsequent reactions.

At the time of the invention, it has in no way been suggested that the monodentate ligand systems presented here make it possible, employed as appropriate catalyst systems in the reductive carbonylation, to obtain such good yields of (hetero)aromatic of in some cases >95% with extremely low by-product spectra, which, compared to the best known system of the prior art ($tBu_3P$), is again a significant improvement.

$(C_1-C_8)$-Alkyl radicals are to be regarded as methyl, ethyl, n-propyl, isopropyl, n-butyl, isobutyl, sec-butyl, tert-butyl, pentyl, hexyl, heptyl or octyl together with all of their bonding isomers.

A $(C_5-C_{20})$-alkyl radical in the context of the definition according to the invention is an appropriate radical having 5 to at most 20 C atoms.

The radical $(C_1-C_8)$-alkoxy corresponds to the radical $(C_1-C_8)$-alkyl with the proviso that this is bonded to the molecule via an oxygen atom.

$(C_2-C_8)$-Alkoxyalkyl means radicals in which the alkyl chain is interrupted by at least one oxygen function, it not being possible for two oxygen atoms to be bonded to one another. The number of carbon atoms indicates the total number of carbon atoms contained in the radical.

A $(C_3-C_5)$-alkylene bridge is a carbon chain having three to five C atoms, this chain being bonded to the molecule considered via two different C atoms.

The radicals just described in the preceding paragraphs can be mono- or polysubstituted by halogens and/or heteroatom-containing radicals having N, O, P, S, Si atoms. These are, in particular, alkyl radicals of the abovementioned type, which have one or more of these heteroatoms in their chain or bonded to the molecule via one of these heteroatoms. The primary, optionally linear $(C_3-C_{20})$-alkyl radical is to be seen in the context of the definition according to the invention as corresponding to the $(C_1-C_8)$-alkyl radical, but where a branching exists at the earliest on the $C_2$, more preferably $C_3$, further preferably $C_4$, very preferably $C_5$, atom or radical.

$(C_1-C_8)$-Acyloxy in the context of the invention is a $(C_1-C_8)$-alkyl radical as defined above having at most 8 C atoms, which is bonded to the molecule via a COO function.

$(C_1-C_8)$-Acyl in the context of the invention is a $(C_1-C_8)$-alkyl radical as defined above having at most 8 C atoms, which is bonded to the molecule via a CO function.

A $(C_6-C_{18})$-aryl radical is understood as meaning an aromatic radical having 6 to 18 C atoms. In particular, these include compounds such as phenyl, naphthyl, anthryl, phenanthryl, biphenyl radicals or systems of the type previously described fused to the molecule concerned, such as, for example, indenyl systems, which can optionally be substituted by $(C_1-C_8)$-alkyl, $(C_1-C_8)$-alkoxy, $(C_2-C_8)$-alkoxyalkyl, $NH(C_1-C_8)$-alkyl, $N((C_1-C_8)$-alkyl$)_2$, OH, $O(C_1-C_8)$-alkyl, $NO_2$, $NH(C_1-C_8)$-acyl, $N((C_1-C_8)$-acyl$)_2$, F, Cl, $CF_3$, $(C_1-C_8)$-acyl, $(C_1-C_8)$-acyloxy, $(C_7-C_{19})$-aralkyl radical, $(C_4-C_{19})$-heteroaralkyl.

A $(C_7-C_{19})$-aralkyl radical is a $(C_6-C_{18})$-aryl radical bonded to the molecule via a $(C_1-C_8)$-alkyl radical.

A $(C_3-C_{18})$-heteroaryl radical in the context of the invention is a five-, six- or seven-membered aromatic ring system of 3 to 18 C atoms, which contains heteroatoms such as, for example, nitrogen, oxygen or sulphur in the ring. Such heteroatoms are in particular to be regarded as radicals such as 1-, 2-, 3-furyl, 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. The heteroaromatics can be substituted in an identical manner to the abovementioned $(C_6-C_{18})$-aryl radicals.

A $(C_4-C_{19})$-heteroaralkyl is understood as meaning a heteroaromatic system corresponding to the $(C_7-C_{19})$-aralkyl radical.

Halogens (Hal) are fluorine, chlorine, bromine, iodine. Hal' is chlorine, bromine, iodine.

EXAMPLES

General Experimental Description

Catalyst and ligand are weighed into an inert Schlenk flask, the solvent is added and the mixture is stirred for about 30 min (preformed). Subsequently, the starting material and the standard (dodecane 0.25 equiv.) are added (GC sample!). Meanwhile, the solid bases are weighed into different 5 ml vials, evacuated a number of times and aerated with argon. The liquid bases are added to the vials via a septum. After this, 2 ml of the substrate-catalyst solution are injected into each vial and mixed with the bases by means of a magnetic stirrer. After this, the vials are placed in the prepared autoclave and this is closed under a stream of argon. After flushing a number of times with synthesis gas, the desired amount of gas can be injected at room temperature, and the autoclave heated. By means of a magnetic stirrer placed underneath, thorough mixing of the individual vials is also guaranteed, insofar as this does not take place adequately by convection. After the reaction, the lukewarm autoclave is additionally cooled below 5° C. in an ice bath and the remaining gas is slowly vented. Subsequently, samples for gas chromatography are taken from the individual vials, filtered through Celite and diluted with ethyl acetate. The determination of the conversions or yield is carried out by means of a separate calibration using commercially obtainable reference compounds. The differences between conversion and yield are mainly to be attributed to the dehalogenated compounds. Reduction to benzyl alcohol or oxidation to benzoic acid was unable to be observed here.

In the following tables, Cn=conversion.

Experiments Carried Out with 4-Trifluoromethylbromobenzene

| Pd(OAc)$_2$ [mol %] | Ligand [mol %] | Base [1.5 equiv] | Solvt. [2 ml] | T [° C.] | t [h] | CO/H$_2$ [bar] | Cn. [%] | CHO [%] | H [%] |
|---|---|---|---|---|---|---|---|---|---|
| 0.33 |  | NEt$_3$ | Toluene | 100 | 4 | 10/10 | 94 | 88 | 5 |
| 0.33 |  | K$_2$HPO$_4$ | Toluene | 100 | 4 | 10/10 | 93 | 83 | 6 |
| 0.33 |  | K$_2$CO$_3$ | Toluene | 100 | 4 | 10/10 | 66 | 56 | 4 |
| 0.33 |  | Cs$_2$CO$_3$ | Toluene | 100 | 4 | 10/10 | 98 | 83 | 8 |

1

| 0.33 |  | NEt$_3$ | Toluene | 100 | 4 | 10/10 | 89 | 84 | 3 |
| 0.33 |  | DABCO | Toluene | 100 | 4 | 10/10 | 85 | 60 | 12 |
| 0.33 |  | K$_2$HPO$_4$ | Toluene | 100 | 4 | 10/10 | 86 | 75 | 3 |

1

-continued

| Pd(OAc)$_2$ [mol %] | Ligand [mol %] | Base [1.5 equiv] | Solvt. [2 ml] | T [°C.] | t [h] | CO/H$_2$ [bar] | Cn. [%] | CHO [%] | H [%] |
|---|---|---|---|---|---|---|---|---|---|
| 0.33 | 1 | NEt$_3$ | NMP | 100 | 4 | 10/10 | 68 | 62 | 3 |
| 0.33 | 1 | DABCO | NMP | 100 | 4 | 10/10 | 89 | 82 | 7 |

Conditions: 6 × 5 ml vials in a 300 ml autoclave having a magnetic stirrer, 2 mmol of starting material, 0.2 equiv. of dodecane (GC standard), 1.5 equiv. of base, 2 ml of solvt.
DABCO ® = 1,4-Diazabicyclo[2,2,2]octane,
DME = Dimethylethylene glycol

Experiments Carried Out with 4-bromoanisole

| Pd(OAc)$_2$ [mol %] | Ligand [mol %] | Base [3 mmol] | Solvt. [2 ml] | T [°C.] | t [h] | CO/H$_2$ [bar] | Cn. [%] | CHO [%] | H [%] |
|---|---|---|---|---|---|---|---|---|---|
| 0.33 | 1 | NEt$_3$ | Toluene | 120 | 4 | 10/10 | 76 | 73 | 0 |
| 0.33 | 1 | NEt$_3$ | NMP | 120 | 4 | 10/10 | 78 | 75 | 0 |
| 0.33 | 1 | N(n-Bu)$_3$ | NMP | 120 | 4 | 10/10 | 68 | 64 | 0 |
| 0.33 | 1 | DABCO | NMP | 120 | 4 | 10/10 | 93 | 82 | 3 |

-continued

| Pd(OAc)$_2$ [mol %] | Ligand [mol %] | Base [3 mmol] | Solvt. [2 ml] | T [°C.] | t [h] | CO/H$_2$ [bar] | Cn. [%] | CHO [%] | H [%] |
|---|---|---|---|---|---|---|---|---|---|
| 0.33 |  1 | NEt$_3$ | Toluene | 140 | 4 | 10/10 | 88 | 85 | 1 |
| 0.33 |  | N(n-Bu)$_3$ | Toluene | 140 | 4 | 10/10 | 94 | 81 | 0 |
| 0.33 |  1 | NEt$_3$ | NMP | 140 | 4 | 10/10 | 97 | 93 | 1 |
| 0.33 |  | N(n-Bu)$_3$ | NMP | 140 | 4 | 10/10 | 96 | 91 | 0 |
| 0.33 |  | DABCO | NMP | 140 | 4 | 10/10 | 85 | 57 | 6 |

Conditions: 6 × 5 ml vials in a 300 ml autoclave having a magnetic stirrer, 2 mmol of starting material, 0.2 equiv. of dodecane (GC standard), 1.5 equiv. of base, 2 ml of solvt.
DABCO ® = 1,4-Diazabicyclo[2,2,2]octane,
DME = Dimethylethylene glycol Experiments Carried Out with 4-bromoanisole

| Pd(OAc)$_2$ [mol %] | n-BuPAd$_2$ [mol %] | Base | Solvt. [2 ml] | T [°C.] | t [h] | CO/H$_2$ [bar] | Cn. [%] | CHO [%] | H [%] |
|---|---|---|---|---|---|---|---|---|---|
| 0.33 | 1 | NEt$_3$ | Toluene | 100 | 16 | 5/5 | 76 | 72 | 0 |
| 0.33 | 1 | DABCO | Toluene | 100 | 16 | 5/5 | 92 | 56 | 18 |
| 0.33 | 1 | DABCO | Toluene | 100 | 44 | 10/10 | 76 | 72 | 0 |
| 0.33 | 1 | NEt$_3$ | Toluene | 100 | 16 | 5/10 | 93 | 44 | 44 |
| 0.33 | 1 | NEt$_3$ | Toluene | 100 | 16 | 1/1 | 77 | 66 | 3 |
| 0.33 | 1 | DABCO | Toluene | 100 | 16 | 1/1 | 89 | 50 | 20 |
| 0.33 | 1 | N(n-Bu)$_3$ | Toluene | 100 | 16 | 2.5/2.5 | 87 | 55 | 0 |
| 0.33 | 1 | K$_2$HPO$_4$ | Toluene | 100 | 16 | 2.5/2.5 | 99 | 58 | 15 |
| 0.33 | 1 | DABCO | Toluene | 100 | 16 | 5/2.5 | 76 | 55 | 0 |
| 0.33 | 1 | N(n-Bu)$_3$ | Toluene | 100 | 16 | 2.5/5 | 99 | 80 | 1 |
| 0.33 | 1 | DABCO | Toluene | 100 | 16 | 2.5/5 | 72 | 28 | 43 |
| 0.33 | 1 | NEt$_3$/pyridine | Toluene | 100 | 16 | 2.5/5 | 100 | 83 | 15 |
| 0.33 | 1 | NEt3 | Toluene | 100 | 16 | 2.5/2.5 | 97 | 92 | 0 |
| 0.33 | 1 | N(n-Bu)3 | Toluene | 100 | 16 | 2.5/2.5 | 98 | 53 | 0 |
| 0.33 | 1 | NEt3/ | Toluene | 100 | 16 | 2.5/2.5 | 79 | 70 | 0 |

-continued

Br-C6H4-OMe → OHC-C6H4-OMe + [H-C6H4-OMe]

| Pd(OAc)₂ [mol %] | n-BuPAd₂ [mol %] | Base | Solvt. [2 ml] | T [° C.] | t [h] | CO/H₂ [bar] | Cn. [%] | CHO [%] | H [%] |
|---|---|---|---|---|---|---|---|---|---|
| 0.33 | 1 | pyridine NEt3/ pyridine | Toluene | 100 | 16 | 2.5/2.5 | 97 | 89 | 0 |
| 0.33 | 1 | NEt3 (1.08) | Toluene | 100 | 16 | 2.5/2.5 | 98 | 90 | 0 |
| 0.33 | 1 | NEt (1.44) | Toluene | 100 | 16 | 2.5/2.5 | 97 | 87 | 0 |
| 0.33 | 1 | NEt3 (2.52) | Toluene | 100 | 16 | 2.5/2.5 | 82 | 76 | 0 |
| 0.33 | 1 | NEt3 (1.0) | Toluene | 100 | 16 | 1/1 | 64 | 54 | 3 |
| 0.33 | 1 | DABCO (1.0) | Toluene | 100 | 16 | 1/1 | 69 | 49 | 12 |
| 0.33 | 1 | TMEDA (1.5) | Toluene | 100 | 16 | 1/1 | 97 | 90 | 2 |
| 0.33 | 1 | TMEDA (0.75) | Toluene | 100 | 16 | 1/1 | 99 | 91 | 3 |
| 0.33 | 1 | TMEDA (0.50) | Toluene | 100 | 16 | 2.5/2.5 | 98 | 92 | 0 |
| 0.33 | 1 | TMEDA (0.75) | Toluene | 100 | 16 | 2.5/2.5 | 98 | 93 | 1 |
| 0.33 | 1 | TMEDA (0.99) | Toluene | 100 | 16 | 2.5/2.5 | 97 | 92 | 0 |
| 0.33 | 1 | TMEDA (1.49) | Toluene | 100 | 16 | 2.5/2.5 | 97 | 92 | 0 |
| 0.33 | 1 | TMEDA (2.48) | Toluene | 100 | 16 | 2.5/2.5 | 97 | 92 | 0 |

Conditions: 6 × 5 ml vials in a 300 ml autoclave having a magnetic stirrer,
2 mmol of starting material, 0.2 equiv. of hexadecane (GC standard), 1.5 equiv. of base
(if not stated otherwise), 2 ml of solvt.
DMGE = N,N-Dimethylglycine ethyl ester, Further Results:

| Aryl bromide [2 mmol] | Pd(OAc)₂ [mol %] | BuPAd₂ [mol %] | TMEDA [eq.] | Toluene [ml] | CO/H₂ [bar] | T [° C.] | t [h] | Conv. [%] | Yield [%] |
|---|---|---|---|---|---|---|---|---|---|
| 4-OMe | 0.25 | 0.75 | 0.75 | 2 | 5 | 100 | 16 | 96 | 92 |
|  | 0.1 | 0.75 | 0.75 | 2 | 5 | 125 | 16 | 100 | 96 |
|  | 0.33 | 1 | 0.75 | 2 | 5 | 100 | 16 | 97 | 93 |
| 4-MeO[30]* | 0.33 | 1 | 0.75 | 2 | 5 | 100 | 16 | 98 | 95 (71 isol.) |
| 3-MeO | 0.25 | 0.75 | 0.75 | 2 | 5 | 100 | 16 | 99 |  |
|  | 0.1 | 0.75 | 0.75 | 2 | 5 | 125 | 16 | 100 |  |
| 2-MeO | 0.25 | 0.75 | 0.75 | 2 | 5 | 100 | 16 | 64 |  |
|  | 0.25 | 0.75 | 0.75 | 2 | 5 | 125 | 16 | 98 |  |
|  | 0.33 | 1 | 0.75 | 2 | 5 | 100 | 16 | 84 |  |
| 4-F | 0.25 | 0.75 | 0.75 | 2 | 5 | 100 | 16 | 98 |  |
|  | 0.1 | 0.75 | 0.75 | 2 | 5 | 125 | 16 | 100 |  |
| 3-F | 0.25 | 0.75 | 0.75 | 2 | 5 | 100 | 16 | 99 |  |
|  | 0.1 | 0.75 | 0.75 | 2 | 5 | 125 | 16 | 100 |  |
| 2-F | 0.25 | 0.75 | 0.75 | 2 | 5 | 100 | 16 | 55 |  |
|  | 0.25 | 0.75 | 0.75 | 2 | 5 | 125 | 16 | 99 |  |
|  | 0.33 | 1 | 0.75 | 2 | 5 | 100 | 16 | 98 |  |
| 4-CF₃ | 0.25 | 0.75 | 0.75 | 2 | 5 | 100 | 16 | 100 |  |
|  | 0.1 | 0.75 | 0.75 | 2 | 5 | 125 | 16 | 100 |  |
| 4-CF₃[30]* | 0.05 | 1 | 0.75 | 30 | 5 | 140 | 16 | 87 |  |
| 4-CN | 0.25 | 0.75 | 0.75 | 2 | 5 | 100 | 16 | 77 |  |
|  | 0.25 | 0.75 | 0.75 | 2 | 5 | 125 | 16 | 100 |  |
|  | 0.33 | 1 | 0.75 | 2 | 5 | 100 | 16 | 99 |  |

-continued

| Aryl bromide [2 mmol] | Pd(OAc)$_2$ [mol %] | BuPAd$_2$ [mol %] | TMEDA [eq.] | Toluene [ml] | CO/H$_2$ [bar] | T [°C.] | t [h] | Conv. [%] | Yield [%] |
|---|---|---|---|---|---|---|---|---|---|
| 4-N(Me)$_2$ | 0.25 | 0.75 | 0.75 | 2 | 5 | 100 | 16 | 99 | |
|  | 0.1 | 0.75 | 0.75 | 2 | 5 | 125 | 16 | 100 | |
| 4-COMe | 0.25 | 0.75 | 0.75 | 2 | 5 | 100 | 16 | 100 | |
| 4-COOMe | 0.25 | 0.75 | 0.75 | 2 | 5 | 100 | 16 | 100 | |
| 4-Cl | 0.25 | 0.75 | 0.75 | 2 | 5 | 100 | 16 | 100 | |
|  | 0.25 | 0.75 | 0.75 | 2 | 5 | 100 | 16 | 100 | |
|  | 0.25 | 0.75 | 0.75 | 2 | 5 | 100 | 16 | 100 | |
|  | 0.25 | 0.75 | 0.75 | 2 | 5 | 100 | 16 | 80 | |
|  | 0.25 | 0.75 | 0.75 | 2 | 5 | 125 | 16 | 100 | |
|  | 0.33 | 1 | 0.75 | 2 | 5 | 100 | 16 | 97 | |
|  | 0.25 | 0.75 | 0.75 | 2 | 5 | 100 | 16 | 99 | |
|  | 0.25 | 0.75 | 0.75 | 2 | 5 | 100 | 16 | 97 | |
|  | 0.25 | 0.75 | 0.75 | 2 | 5 | 100 | 16 | 83 | |
|  | 0.25 | 0.75 | 0.75 | 2 | 5 | 125 | 16 | 100 | |
|  | 0.33 | 1 | 0.75 | 2 | 5 | 100 | 16 | 100 | |

*Data mmol

The invention claimed is:

1. A process for the preparation of (hetero)aromatic aldehydes comprising:

reacting a halogen-substituted (hetero)aromatic compound, with CO and H$_2$ in the presence of a base and a palladium catalyst having a monodentate phosphane ligand of the general formula (I)

wherein $R^1$ and $R^2$ independently of one another are (C$_5$-C$_{20}$)-alkyl, where the C atom which is bonded to phosphorus is a tertiary centre, and $R^3$ is a primary, optionally linear (C$_3$-C$_{20}$)-alkyl radical.

2. The process according to claim 1, wherein the base is an inorganic or organic base.

3. The process according to claim 1, wherein the reacting optionally comprises a solvent selected from the group consisting of NMP (N-methylpyrrolidone), DMGE (dimethyl glycol ether), hexane, heptane, octane, toluene, xylene, anisole, DMF (dimethylformamide), DMAC (dimethylacetamide), 1,4-dioxane, MTBE, THF, acetonitrile, benzonitrile, ethyl acetate, isopropyl acetate, dibutyl ether, dimethyl carbonate, diethyl carbonate, and dipropyl carbonate.

4. The process according to claim 1, wherein a CO pressure is from 0.05 to 10 MPa.

5. The process according to claim 1, wherein a molar ratio of CO to H$_2$ is in the range from 5:1 to 1:5.

6. The process according to claim 1, wherein a mol % of catalyst based on moles of (hetero)aromatic is from 0.001 mol % to 10 mol %.

7. The process according to claim 1, wherein a palladium:phosphane molar ratio is from 1:0.1 to 1:20.

8. The process according to claim 1, wherein a temperature of the reacting is in the range from 70 to 170° C.

9. The process according to claim 1, wherein $R^1$ and $R^2$ are polycyclic radicals.

10. The process according to claim 9, wherein $R^1$ and $R^2$ are each an adamantyl radical.

11. The process according to claim 10, wherein $R^3$ is a n-alkyl radical selected from the group consisting of n-butyl, n-pentyl and n-hexyl.

12. The process according to claim 11, wherein $R^3$ is n-butyl.

* * * * *